United States Patent [19]

Lambert et al.

[11] Patent Number: 5,361,624
[45] Date of Patent: Nov. 8, 1994

[54] SENSOR FOR DISSOLVED AIR IN BRAKE FLUID AND METHOD OF USING THE SAME

[75] Inventors: David K. Lambert, Sterling Height; Mark W. Verbrugge, Troy; Brian J. Koch, Northville, all of Mich.

[73] Assignee: General Motors Corporation, Detroit, Mich.

[21] Appl. No.: 144,382
[22] Filed: Nov. 2, 1993
[51] Int. Cl.$^5$ .............................. G01N 27/26
[52] U.S. Cl. ........................ 73/19.1; 204/431
[58] Field of Search .................. 73/19.1, 19.01; 204/424, 426, 431

[56] References Cited

U.S. PATENT DOCUMENTS

| | | | |
|---|---|---|---|
| 3,223,608 | 12/1965 | Hersch | 204/431 |
| 3,521,478 | 7/1970 | Megorien | 73/19.05 |
| 4,853,091 | 8/1989 | Mund et al. | 204/431 X |
| 5,215,644 | 6/1993 | Ashikaga | 204/431 X |

FOREIGN PATENT DOCUMENTS 894370  4/1962  United Kingdom ................. 73/19.1

OTHER PUBLICATIONS

D. R. Baker and M. W. Verbrugge, "An analytic solution for the microdisk electrode and its use in the evaluation of charge-transfer rate constants," J. Electrochem. Soc. 137,3836 (1990).
A. J. Bard and L. R. Faulkner, *Electrochemical Methods*, (Wiley, New York, 1980), pp. 137–208.
N. J. Clark, "The effect of brake system evacuation and fill on initial brake pedal travel," S. A. E. Paper 910574 (1991).
H. L. Clever and R. Battino, "The solubility of gases in liquids," in *Solutions and Solubilities*, edited by M. R. Dack (Wiley, New York, 1975), pp. 379–441.
E. V. Galinker, "Vacuum measuring cell with a microelectrode," Élektrokhimiya 26, 752 (1990) [Soviet Electrochemistry 26, 673 (1990)].
E. L. Haines, "Water in brake fluid by differential near infrared," S. A. E. Paper 720057 (1972).
J. P. Hoare, *The Electrochemistry of Oxygen*, (Wiley, New York, 1968), pp. 153–210.
K. Kinoshita, *Electrochemical Oxygen Technology*, (Wiley, New York, 1992), pp. 5–15.
C. Lamy, "Electrocatalytic oxidation of organic compounds on noble metals in aqueous solution," Electrochim. Acta 29, 1581 (1984).
S. S. Lord, Jr., and L. B. Rogers, "Polarographic studies with gold, graphite, and platinum electrodes," Anal. Chem. 26, 284 (1954).
V. G. Magorien, "Apparatus for measuring gases dissolved in liquids," U.S. Patent 3,521,478 (21 Jul. 1970).
M. Palys, Z. Stojek, and Z. Kublik, "Use of submicroelectrodes in rapid determination of dissolved oxygen by an absolute, computer-aided cronoamperometric method," Chemia Analityczna 37,25 (1992).
S. Pons and M. Fleischmann, "Introduction and overview," in *Ultramicroelectrodes*, edited by M. Fleischmann, S. Pons, D. R. Rolison, and P. P. Schmidt (Datatech Systems, Morganton, North Carolina, 1987), pp. 1–16.
M. Urano, "Development of brake fluid vacuum supply system," S. A. E. Paper 871265 in it Proceedings of the Fourth International Pacific Conference on Automotive Engineering, (SAE Australasia, Melbourne, Australia, 1987), p. 265.1.
M. W. Verbrugge and D. R. Baker, "Transient diffusion and migration to a disk electrode," J. Phys. Chem. 96,4572 (1992).
E. Yeager, "Electrocatalysis for $O_2$ Reduction," Electrochim. Acta 29,1527 (1984).

Primary Examiner—Thomas P. Noland
Assistant Examiner—Joseph W. Roskos
Attorney, Agent, or Firm—Cary W. Brooks

[57] ABSTRACT

The present invention includes a microelectrode which achieves a surface-renewal advantage. The sensor and method directly controls the oxidizing and reducing nature of the electrode interface by controlling the cell potential, thereby protecting the sensing electrode's surface during periods in which the sensor is not being used. The microelectrode is biased at a small positive potential relative to the counterelectrode, except when a measurement is desired. To measure oxygen concentrations in brake fluid, the microelectrode is biased at a greater potential and the current is measured. After the current measurement, the potential is returned to the small positive potential. The oxygen concentration (and thus the amount of air) in the brake fluid is linearly related to the current measured.

4 Claims, 4 Drawing Sheets

SENSOR FOR DISSOLVED AIR IN BRAKE FLUID AND METHOD OF USING THE SAME

FIELD OF THE INVENTION

This invention relates to a sensor for determining the amount of air in brake fluid, and more particularly, to a sensor using a microelectrode to measure the amount of oxygen in brake fluid.

BACKGROUND OF THE INVENTION

The mass assembly of automotive and truck vehicles includes the filling of braking devices with brake fluid. This includes the step of using a vacuum pump to first remove air from the vehicle hydraulic system associated with the braking device. Next, pressurized brake fluid is allowed to flow into the hydraulic system. Finally, the hydraulic system and braking device are tested. This procedure is standard in the industry.

For the brakes to work properly, there cannot be bubbles in the hydraulic system. Some residual gas remains in the brake system after pumping that must be absorbed into the brake fluid. Brake fluid arrives at the assembly plant saturated with dissolved air. Consequently, if the as-received fluid is used without processing, it cannot dissolve the residual air, and bubbles end up in the hydraulic system. To eliminate bubbles, dissolved air is removed from the brake fluid before it is used by dripping the fluid through a vacuum chamber maintained at a pressure <1 kPa. The deaerated fluid at the bottom of the chamber is pumped into a high pressure (about 100 psi) line and piped to the fluid-fill station. It is possible, however, for subtle equipment malfunctions to short circuit the air removal process or introduce air into the brake fluid. For example, if a pump has a bad seal, then air is injected into the high pressure line.

After the brake system has been filled with fluid, it is tested for leaks or air bubbles. Force is applied to the brake system's primary piston, and the piston's motion is monitored. A leak in the brake system causes the piston to move slowly after the initial compressive displacement, while a bubble affects the initial displacement. Even without bubbles, the initial displacement measured for a group of properly functioning vehicles can have a large amount of scatter. This makes it difficult to identify the extra displacement caused by bubbles as something new when it first appears. Consequently, bubble-related problems are not easily diagnosed by the initial displacement. Also, excessive initial piston displacement may be symptom of brake-system problems other than excessive air content. Consequently, the diagnosis of problems in the brake-processing equipment can represent a difficult endeavor, and an unambiguous measurement of air content in brake fluid would be desirable.

A malfunction that causes the assembly plant to produce vehicles with air bubbles in the brake lines is very serious. Because proper functioning of a vehicle's brakes is essential for safety, each vehicle produced with air in the brake lines must later have the air bled out before the vehicle can be shipped.

Dissolved gas in liquids is often detected in one of two ways: (1) the gas is phase separated into a bubble, the volume of which is measured, or (2) by an electrochemical method. As currently practiced to detect air in brake fluid, however, both techniques employ mercury, which makes their application questionable in a vehicle-assembly plant. Small quantities of a particular dissolved gas can also be detected by bubbling a carrier gas through a liquid and using standard analytical techniques to detect the species of interest in the carrier gas.

Volumetric methods to measure dissolved gas in liquids have been used in the past. A device is available "to determine free, entrained, and dissolved air in hydraulic and other fluids." The device consists of a transparent container and a manually operated vacuum pump that uses mercury as the working fluid. A sample of the fluid is placed in the container. The pressure on the fluid is reduced to near zero with the hand operated vacuum pump. The dissolved air forms bubbles, which rise to the top of the container. The change in the liquid level indicates how much dissolved air was present in the liquid.

Electrochemical methods to detect dissolved oxygen in liquids have been known. Because aqueous (water based) solutions are of the greatest practical importance, most electrochemical sensors have been developed for use in water. In particular, the Clark oxygen sensor, developed to measure dissolved oxygen in blood, is widely available. Another important technique is polarography with the dropping mercury electrode. This laboratory technique is presently used by brake fluid manufacturers to analyze samples of brake fluid for dissolved oxygen.

Polarography makes use of the potential difference that can be maintained over atomic dimensions at the interface between an electrode and an electrolyte. For each molecule that reacts, a known amount of charge passes through the circuit. Current is measured versus the applied potential difference. For small potential bias, the current increase is usually linear and moderate. As the potential bias is increased, the reaction rate and the corresponding current increase exponentially with the potential difference associated with the interface (i.e., the surface overpotential). As the potential difference is increased further, reaction resistance at the surface stops being the rate limiting step. All of the molecules that reach the surface react, which gives rise to a current that is limited by the rate at which fresh reactant is brought to the surface by convection and diffusion, a condition known as being transport limited. The great advantage of the dropping mercury electrode over other forms of polarography is that the working-electrode surface is continually renewed. A common problem with solid electrodes is that a film develops on the electrode that eventually influences the electrode behavior.

Thus, heretofore there has been a need for a device and method of reliably determining the amount of air or gas in brake fluid which overcomes the shortfalls of the prior art.

SUMMARY OF THE INVENTION

The present invention includes a microelectrode and a potential control strategy that avoids the electrode degradation that would occur if the measurement were performed continuously. The sensor and method directly controls the oxidizing and reducing nature of the electrode interface by controlling the cell potential, thereby protecting the sensing electrode's surface during periods in which the sensor is not being used. The microelectrode is biased at a positive (anodic) potential (preferably +0.1 V) relative to the counterelectrode, except when a measurement is desired. To measure oxygen concentrations in brake fluid, the microelectrode is biased at a negative (cathodic) potential (preferably about −1.5 V) for a predetermined internal (preferably 10 seconds) and the current is measured. After the current measurement, the potential is returned to the small positive potential. The oxygen concentration (and thus the amount of air) in the brake fluid is linearly related to the current measured.

These and other objects, features and advantages of the present invention will be apparent from the following brief description of the drawings, detailed description and appended claims and drawings.

DETAILED DESCRIPTION

The present sensor is intended to avoid bubbles in the assembled brake systems by periodically monitoring the oxygen concentration in the brake fluid. Since air is 21% oxygen, a sensor that detects dissolved oxygen is able to alert plant personnel to the presence of an unacceptable amount of dissolved air in the brake fluid. If a failure occurs gradually, the sensor may be able to signal the need for repair in time to schedule preventative maintenance. Repair time would also be reduced if the assembly plant had a way to diagnose the problem.

Figure 1:
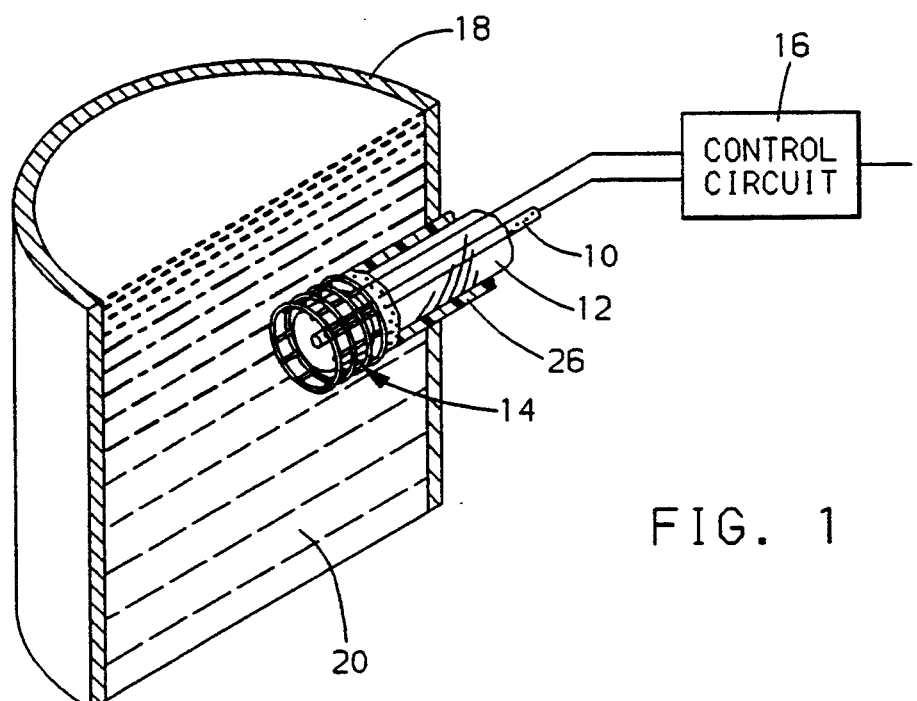
FIG. 1 is a schematic view of a sensor to measure dissolved oxygen in brake fluid according to the present invention.

The sensor that we have developed to measure dissolved air in brake fluid is shown schematically in FIG. 1. The sensor consists of a carbon microdisk electrode 10 surrounded by glass 12, a counterelectrode 14, both of which are submerged in a container 18 having brake fluid 20 therein and a circuit 16. In one embodiment, the potential between the carbon microelectrode 10 and the platinum screen counterelectrode 14 is controlled and the resulting current is the sensor signal. In another embodiment, the platinum screen is omitted, the potential between the carbon microelectrode and the (metallic) container is controlled, and the resulting current is the sensor signal. The microdisk electrode is a small diameter (less than 100 micron) filament, preferably carbon, in a larger diameter (about 4 mm) glass rod.

In FIG. 1, the carbon filament is electrically connected to an external circuit. The circuit maintains the microdisk electrode at a potential in the range of 0 to +3 V, but preferably at +0.1 V, relative to the counterelectrode at all times except during a measurement cycle. When a measurement of oxygen concentration is desired, a potential ranging from −0.1 to −3 V and preferably −1.5 V is first applied to the microdisk electrode relative to the counterelectrode to begin the cycle. After a fixed delay time (10 seconds is suitable) the current is measured. The current measured at this time is the sensor's output. After the current measurement is completed the microdisk electrode's potential is returned to +100 mV relative to the counterelectrode to await the next measurement cycle.

Figure 2A:
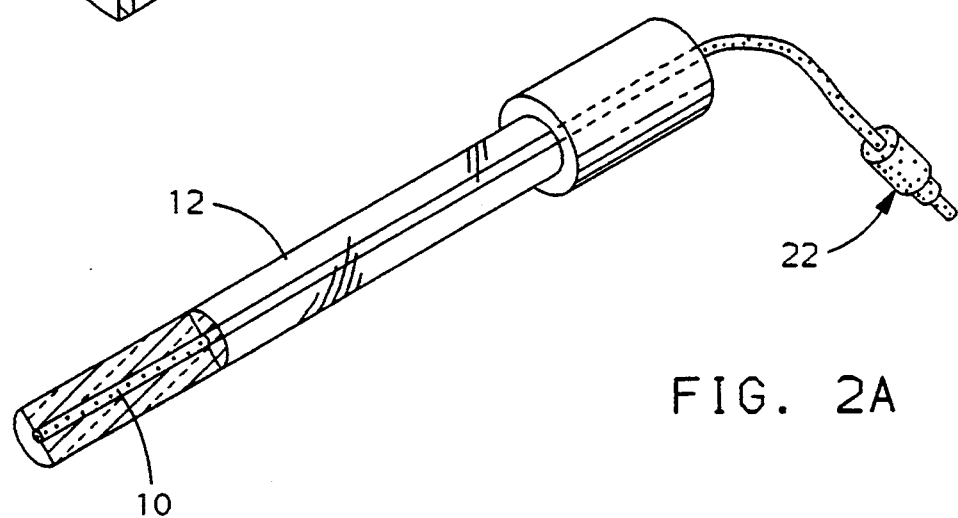
FIGS. 2a and 2b are illustrations of a microelectrode and electrode assembly useful in measuring dissolved oxygen in brake fluid according to the present invention.
Figure 2B:
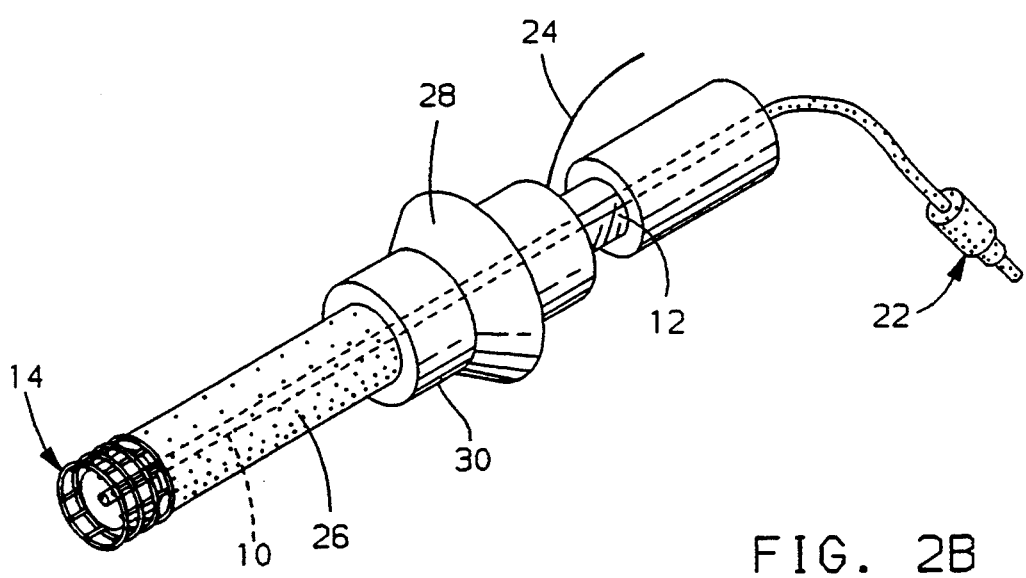

The physical form of a suitable sensor is shown in FIGS. 2a and 2b. A suitable microdisk electrode, shown in FIG. 2a, is part number MF-2007 available from Bioanalytical Systems, West Lafayette, Ind. It consists of a 10 μm diameter carbon filament 10 sealed in a 4 mm diameter glass rod 12. An electrical connector 22 is provided to the carbon fiber. The electrode is prepared by polishing with 0.3 μm alumina, rinsing with dilute nitric acid, and rinsing liberally with purified water. The electrode assembly is shown in FIG. 2b. The counterelectrode is platinum screen 14 that is wrapped around the end of the microelectrode. A platinum wire 24 woven into the screen makes electrical contact and extends out the back of the sensor. Heat shrink tubing 26 such as Teflon is used to fasten the platinum screen and wire to the microelectrode and electrically insulate them from the metal fittings. A piece of Teflon tubing 30 is slid over this assembly to provide a seal inside a ¼ inch compression fitting (metal ferrule 28). In the plant, the sensor assembly is screwed into a pipe that carries the brake fluid.

It should be recognized that the nature of the counterelectrode is of only secondary importance, and, in fact, the outer conductive housing (stainless steel for example) can be used as the counterelectrode, simplifying sensor construction. It is critical, however, that the chemical properties of the counterelectrode surface remain invariant to the extent that the counterelectrode does not alter the sensor's signal.

We can view the reaction at the microelectrode surface as

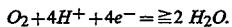

$$O_2 + 4H^+ + 4e^- = \geq 2\, H_2O.$$

As the potential of the carbon filament relative to the counterelectrode is scanned from equilibrium (0 V) to more negative values, electrons are forced to the electrode surface. As a result, the rate of the reduction reaction increases, as does the flux of soluble oxygen to the electrode. Eventually, as the potential of the carbon filament becomes more negative, the flux of soluble oxygen to the carbon filament becomes transport limited. Consequently the current versus voltage approaches a limiting value. A potential of −1.5 V is an acceptable value for transport limited operation. The sensor measures the current under the conditions for transport limited operation. The measured current is proportional to the concentration of dissolved oxygen in the fluid.

Figure 3:
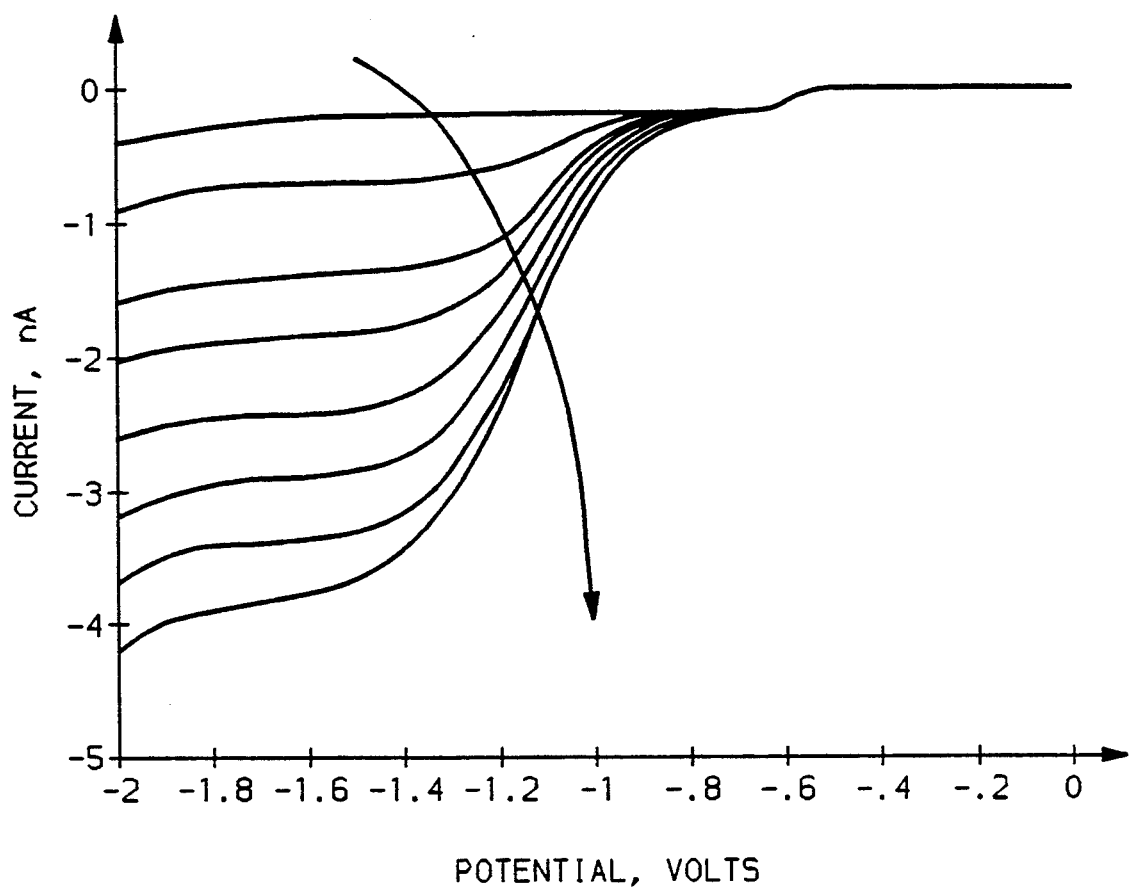
FIG. 3 is a graphic illustration of voltammograms obtained by measuring brake fluid with up to 21% oxygen dissolved therein using a carbon microelectrode sensor according to the present invention.

The response of the sensor to the oxygen concentration in brake fluid is shown in FIG. 3. This shows the results of a series of experiments in which the sensor was used to measure the current versus potential for DELCO SUPREME 11 brake fluid. The experiment was repeated with a series of oxygen concentrations in the solution. The oxygen concentration was controlled by the oxygen concentration in the mixture of oxygen and nitrogen that was bubbled through the brake fluid at atmospheric pressure. It is well known that in this situation the concentration of dissolved oxygen in the brake fluid is proportional to the concentration of oxygen in the gas being bubbled through the fluid. The arrow in FIG. 3 is drawn to note the influence of increasing oxygen concentration of 0, 3, 6, 9, 12, 15, 18 and 21 percent oxygen.

Several different circuits have been successfully used to control the potential of the microelectrode and measure the current: a 1.5 V battery as current source together with a resistive divider and a Keithley model 485 picoammeter, an EG&G Princeton Applied Research potentiostat/galvanostat model 273, and a Bioanalytical Systems model CV 27 voltammograph interfaced to a PA-1 preamplifier. Potential scans were conducted at 25 mV/s.

The potential of the microdisk electrode cannot simply be held at $-1.5$ V for long periods of time. It was found that after the electrode had been held at $-1.5$ V for two days, the sensor's current had decayed to less than 10% of its transport-limited value. A likely explanation for the observed decay is that organic species adsorb on the surface. With an electrochemical sensor the potential directly controls whether the interface is oxidizing or reducing. Thus oxygen can be reduced when it is desired to monitor the oxygen concentration, and the surface can be returned to an oxidizing condition when the sensor is not in use. It was observed that if the potential is maintained at 100 mV (positive, oxidizing) for the majority of the time the sensor is in the brake fluid, then the potential can be occasionally changed to negative values to briefly sense oxygen without causing a significant decay of the current. After the sensor had been operated in this way for two weeks it continued to give stable, reproducible oxygen measurements.

Figure 5:
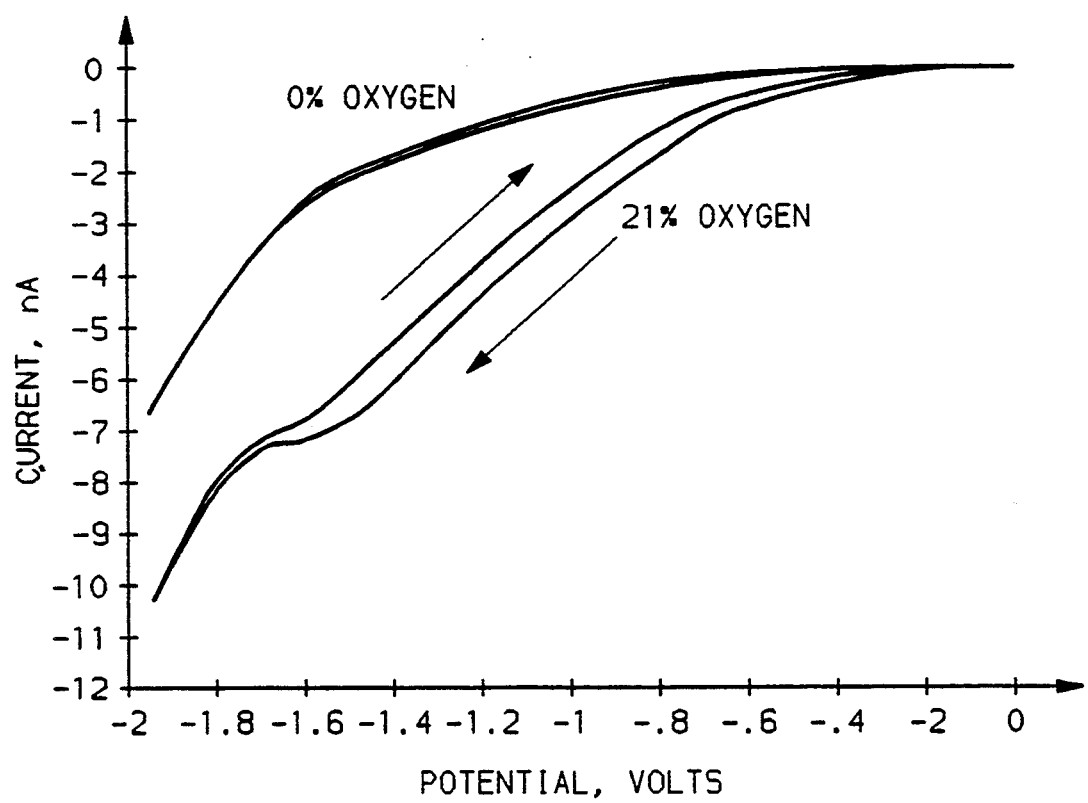
FIG. 5 is a graphic illustration of current versus voltage using a platinum microelectrode to detect oxygen in brake fluid instead of the preferred carbon microelectrode.

The material used for the microdisk electrode is important. Platinum, a commonly employed and highly catalytic electrode material for oxygen reduction, is an unacceptable substitute for carbon. With a platinum microdisk, the voltammograms depend on the potential-scan direction as shown in FIG. 5. The voltammograms shown here are analogous to those shown in FIG. 3, but were obtained with a 10 μm diameter platinum microdisk electrode. Arrows indicate the potential-scan direction; scanning from the equilibrium potential (0 volts) yields a larger current than does the scan back to 0 volts. No such hysteresis is seen in voltammograms with carbon microdisk electrodes. Carbon is less catalytic to the reaction of organic and hydrogen-containing species that adsorb on the electrode surface than platinum. This difference results in better performance with carbon compared with platinum.

Figure 4:
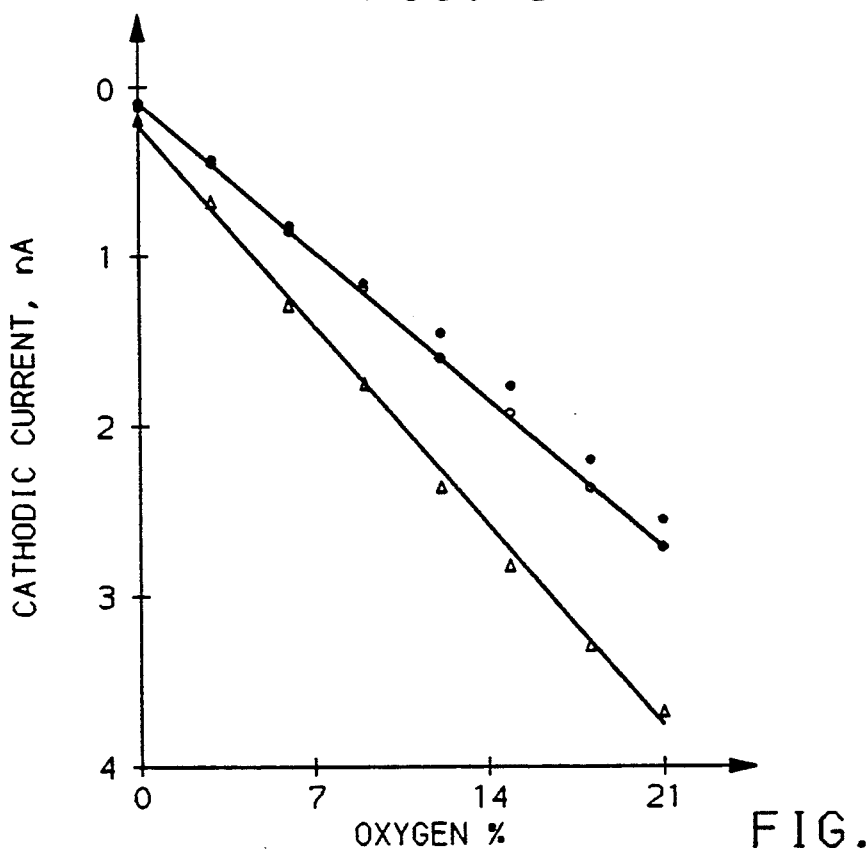
FIG. 4 is a graphic illustration of measured current from the sensor (at −1.5 V cathodic bias) versus molar fraction of oxygen in the gas bubbled through the brake fluid (for three different samples of brake fluid), measured according to the present invention.

The influence of water in the brake fluid on the measured oxygen concentration was also checked. Brake fluid absorbs water from the ambient air, but the concentration of water in the brake fluid is limited as part of the quality control process. As shown in FIG. 4, the effect of water is small even with a concentration of 1 mol/L water in brake fluid. For three different samples of brake fluid, FIG. 4 shows the transport-limited current measured versus oxygen mole percent concentration in the gas bubbled through the fluid. The data plotted as triangles (Δ) was obtained with DELCO SUPREME 11 brake fluid. The data plotted as open circles (○) was obtained with "as received" SOLDER SEAL GUNK (registered trademark) brake fluid. The data plotted as filled circles (●) was obtained with SOLDER SEAL GUNK brake fluid to which enough water had been added to increase the water concentration by 1 mol/L. Both the solder Seal Gunk brake fluid and the DELCO SUPREME 11 brake fluid are glycol base brake fluids sold for dot3 applications. The SOLDER SEAL GUNK brake fluid was in a 12 fl. oz. can that indicated that it was manufactured for Radiator Specialty Company, Charlotte, N.C. 28234. The DELCO SUPREME 11 brake fluid was supplied by the Delco Chassis Division of General Motors Corporation. Lines drawn through the data (Δ and ○) were fit by the method of least squares. Car manufacturers specify that the glycol base brake fluid used to fill the brake lines in assembly plants should have a boiling point of at least 416 degrees F. or greater. Data of boiling point versus water concentration of several different types of glycol base brake fluid is given in FIG. 3 of E. L. Haines, "Determination of water in brake fluid by differential near infrared," SAE Paper 720057 (1972). The boiling point versus water concentration depends on the type of brake fluid, but the water concentration will be no more than 1% by volume (0.56 mol/L) if the brake fluid has a high enough boiling point to meet car manufacturers' specifications. Consequently water in the brake fluid will not cause a significant error in the sensor's response to dissolved oxygen.

To achieve the surface-renewal advantage of the dropping mercury electrode, often one can control directly the oxidizing or reducing nature of the interface by controlling the cell potential, thereby protecting the sensing electrodes; surface during periods in which the sensor is not being used. Thus, it is necessary to bias the microelectrode at a small positive potential ($+0.1$ V), relative to the counterelectrode, except when a measurement is desired. To measure oxygen concentrations, the microelectrode is biased at $-1.5$ V, and after a 10-second delay the current is measured. After the current measurement, the potential is returned to the positive potential. The oxygen concentration in the brake fluid is linearly related to the measured current after the 10-second delay.

EXAMPLE

In this example, two brake fluids were examined:
SOLDER SEAL GUNK (registered trademark), part no. M44-12, Dot3, 12 fl. oz. can, manufactured for Radiator Specialty Company, Charlotte, N.C. 28234;
DELCO SUPREME 11, #1052535, Dot3, Delco Moraine Division, GMC, 1420 Wisconsin Blvd., P.O. Box 1245, Dayton, Ohio 45401.

The specific chemical constitution of the SOLDER SEAL brake fluid is not known although its physical properties resemble those of the DELCO SUPREME 11, which is composed primarily of polyalkylene glycols (22%) and polyethylene glycol ethers (77%). Other minor constituents (less than 1%) are alkenyl succinic anhydride, benzotriazole, and secondary alkylamines.

Blends of gaseous oxygen and nitrogen (Scott Specialty Gases) were bubbled through the solutions to control the concentration of soluble oxygen.

The electrochemical cells were controlled by either an EG&G Princeton Applied Research Potentiostat/Galvanostat Model 273 or a Bioanalytical Systems CV-27 Voltammograph interfaced to a PA-1 Preamplifier. Potential scans were conducted at 25 mV/s, a scan rate slow enough to ensure that pseudosteady-state mass-transport conditions prevailed. Platinum and carbon microdisk electrodes of 10-μm diameter were purchased from Bioanalytical Systems. The electrodes were polished with 0.3-μm alumina, rinsed with dilute nitric acid, and rinsed liberally with purified water. A platinum screen served as the counter and reference electrode. Experiments were conducted in a Faraday cage. A Nicolet 4094B Storage Oscilloscope was used to collect the current and potential data for storage onto floppy disks.

The potential of the carbon microdisk electrode, relative to the platinum screen, was scanned linearly from 0 to $-2$ volts. The resulting current-potential plot (voltammogram) for the DELCO SUPREME 11 brake fluid is shown in FIG. 3. The arrow indicates increasing oxygen concentration. Negative currents denote cathodic processes. We can view the oxygen reduction reaction as $$O_2 + 4H^+ + 4e^- = 2H_2O$$

As the potential is scanned from equilibrium (0 volts) to more negative values, electrons are forced to the electrode surface, and the reduction reaction rate increases. When the reaction rate becomes limited by the transport of soluble oxygen to the interface, the current acquires a limiting value. As is shown in FIG. 3, the transport-limited current increases with soluble oxygen concentration in the bulk fluid. Between the equilibrium (open-circuit) and transport-limited conditions, interfacial kinetics influence the current-potential relationship. The region of the voltammogram governed by interfacial kinetics is often described by a Butler-Volmer equation. By solving the governing partial differential equation for the reactant material balance, one can express analytically the transport-limited current $I_{lim}$ as $$I_{lim} = -4nFDc^{bulk}a$$
$$= -4nFDKpa,$$

where a is the disk radius n denotes the number of electrons per reaction (4 for Eq. 1), and F is Faraday's constant. The soluble-oxygen diffusion coefficient, bulk concentration, and inverse Henry's Law constant are given by D, $c^{bulk}$, and K, respectively. The oxygen partial pressure in the gas stream is denoted by p.

The symbols shown in FIG. 4 correspond to the transport-limited current for various oxygen contents, obtained by varying the oxygen content in the gas stream between 0 and 21 mole percent. These data were obtained by holding the potential constant at $-1.5$ volts and reading the resulting pseudosteady-state current.

Water is the primary contaminant in the brake fluid that can be reduced electrochemically. We checked to make sure that co-reduction of contaminant water with soluble oxygen does not render the sensor ineffective for monitoring purposes. The water concentration in brake fluid is already controlled since the boiling point of brake fluid decreases with increasing water concentration. Some manufacturers specify that the glycol base brake fluid used to fill the brake lines in assembly plants should have a boiling point of at least 416° F. Several experiments were completed with water contents ranging between 0 and 1 mol/L. The 1-mol/L results are shown in FIG. 4, where it is seen that this concentration of water does not affect significantly the response and should not present additional difficulty in implementing the microdisk sensor for oxygen detection purposes. Using an analogous set of experiments, we found that the same insensitivity to water is obtained with DELCO SUPREME 11 brake fluid.

FIG. 4 shows that at the same oxygen partial pressure, the current observed with DELCO SUPREME 11 brake fluid is more negative than with SOLDER SEAL brake fluid. The difference could be caused either by a larger soluble-oxygen concentration in DELCO SUPREME 11 brake fluid for the same oxygen partial pressure, or by a larger soluble-oxygen diffusion coefficient for DELCO SUPREME 11 brake fluid.

In FIG. 3 there is a small oxygen-independent step at $-0.5$ V in the voltammogram in addition to oxygen-dependent step at $-1.1$ V. The oxygen-independent step is caused by the reduction of some species other than oxygen, possibly the secondary amines in the brake fluid. Since it is small, it does not interfere with the oxygen measurement.

Figure 6:
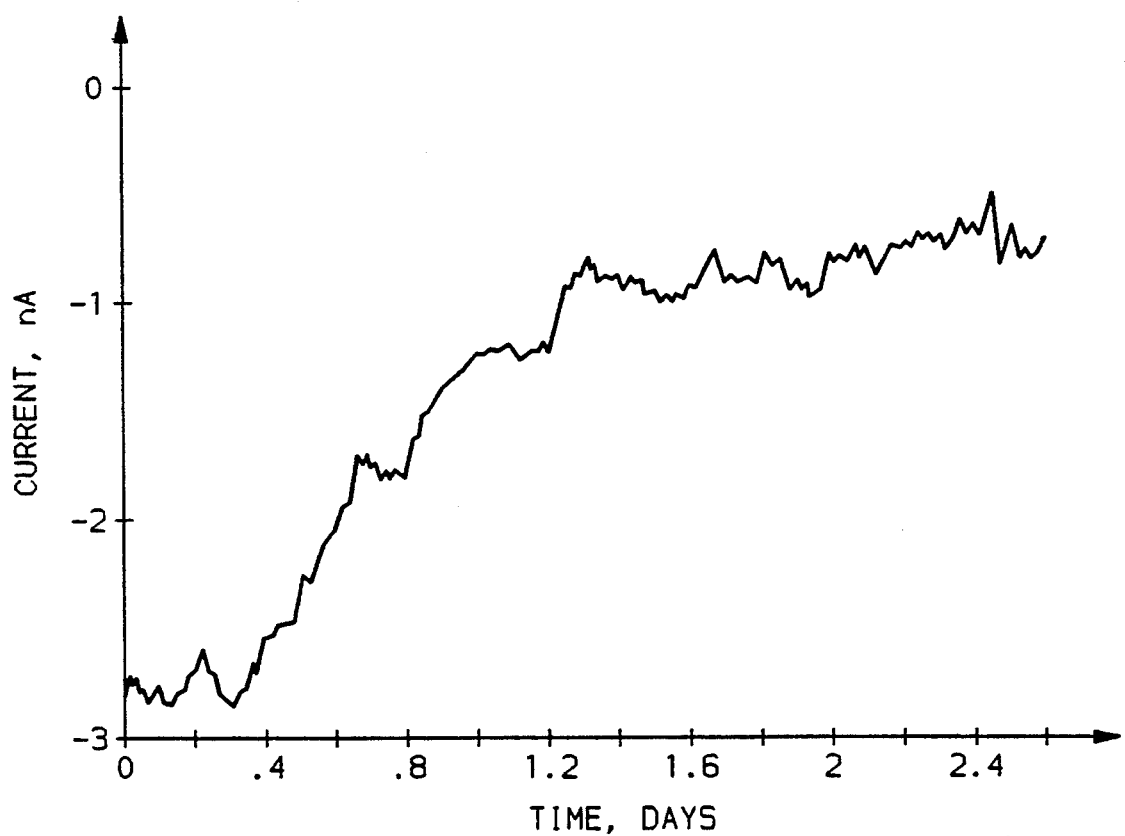
FIG. 6 is a graphic illustration showing the long term decay in measured current versus time when the potential applied to the microelectrode is maintained at −1.5 V instead of following the procedure described in the present invention.

The carbon surface of the microdisk can be altered by adsorption of solution species. It was found that if the potential was held at $-1.5$ V for two days, the sensor current eventually decays from its transport-limited value. An example of this phenomenon is shown in FIG. 6, where the current response to a potential of $-1.5$ V is plotted against time. The current magnitude is seen to decay from its transport-limited value (near $-3$ nA) after a half day of operation. Since the absolute value of the cell-current decays to well below its transport-limited value, this mode of operation is not suitable for a sensor.

Figure 7A:
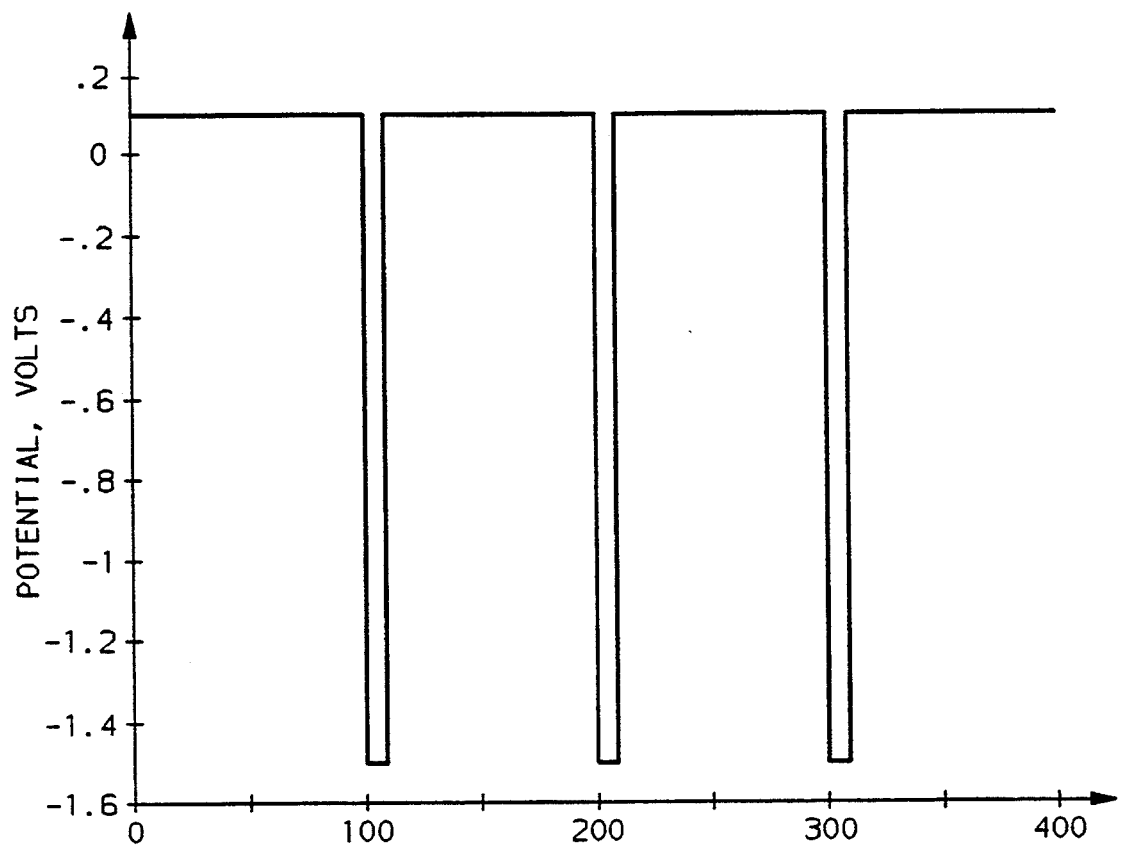
FIGS. 7A and 7B are graphic illustrations showing the potential excitation when the potential of the microelectrode is controlled according to the present invention (FIG. 7A), and the corresponding current response with 21 mole percent oxygen in nitrogen bubbled at atmospheric pressure through DELCO SUPREME 11 brake fluid (FIG. 7B).
Figure 7B:
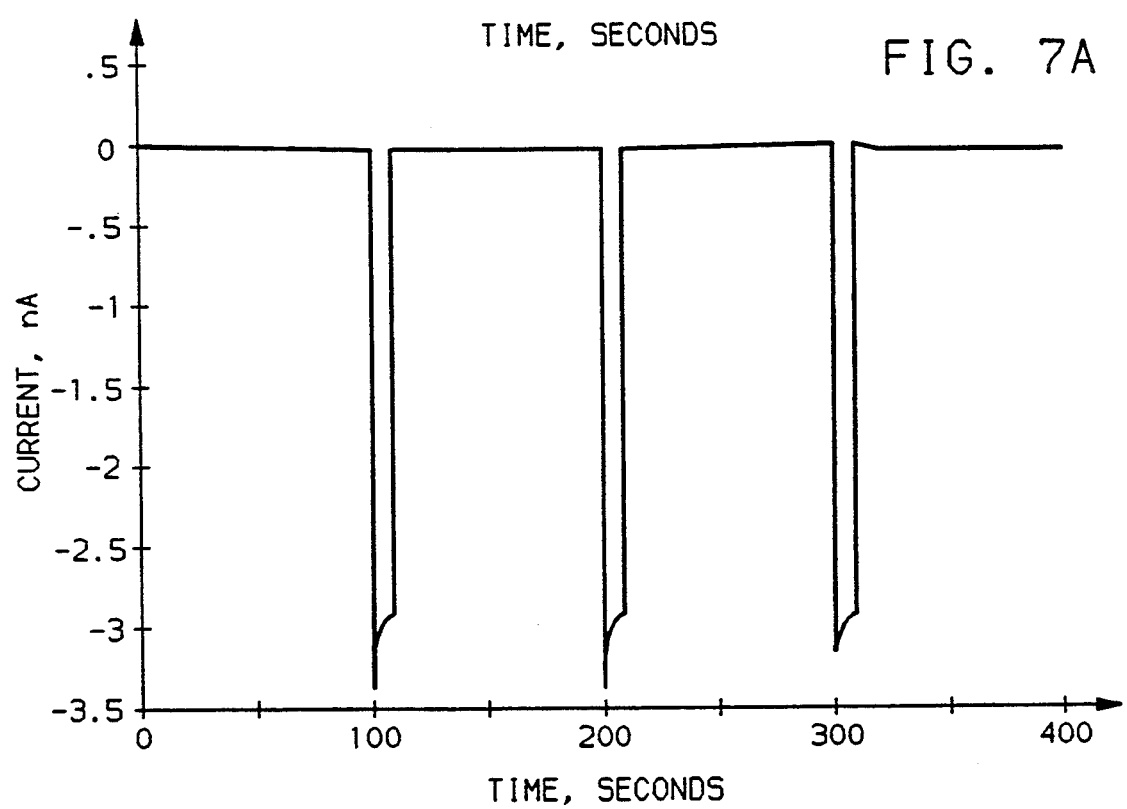

A unique advantage of electrochemical sensors is that it is possible to control directly the oxidizing or reducing nature of the interface. Thus one can reduce oxygen when it is desired to monitor the oxygen concentration, and return the interface to an oxidizing condition when the sensor is not in use. When in the oxidizing condition, organic species that might otherwise occlude the surface do not adsorb, and a stable and uniform current response results when the potential is set to reduce soluble oxygen. The data in FIGS. 7A and 7B result from a such a regime. We found that if the potential is maintained at 100 mV (positive, oxidizing) for the majority of the time in which the sensor is placed in the brake fluid, then the potential could be turned briefly to negative values to sense oxygen, and no significant current decay results. Stable, reproducible cathodic currents were obtained using this regime for over two week of sensor operation.

The embodiments of the invention in which an exclusive property or privilege is claimed as defined as follows:

1. A method of in situ monitoring the concentration of oxygen in hydraulic brake fluid comprising:
   a) placing a microelectrode and a counterelectrode in contact with brake fluid used in a continuous hydraulic brake fluid filling operation;

b) applying a negative potential to the microelectrode relative to the counterelectrode of an amount sufficient so that the flux of soluble oxygen to the microelectrode is transport limited and thereafter measuring the current;

c) applying a positive potential to the microelectrode of an amount sufficient to retard film development on the microelectrode during periods other than when step (b) is being performed; and repeating steps (b)-(c).

2. A method as set forth in claim 1 wherein said microelectrode comprises a microdisk comprising a carbon filament.

3. A method as set forth in claim 1 further comprising the step of adjusting the concentration of oxygen in said hydraulic brake fluid wherein the current measured in step (b) is within a predetermined range.

4. A method as set forth in claim 1 wherein the counterelectrode comprises a metal container used to hold the hydraulic brake fluid.

* * * * *